United States Patent
Zelka

(10) Patent No.: US 11,903,323 B2
(45) Date of Patent: Feb. 13, 2024

(54) STRAP HAVING A PORTION OF ELECTRO-ACTIVE POLYMER, METHODS AND MECHANISMS FOR MAKING AND USING THE SAME

(71) Applicant: Elastimed Ltd., Yokneam Ilit (IL)

(72) Inventor: Omer Zelka, Kfar-saba (IL)

(73) Assignee: Elastimed Ltd., Yokneam Ilit (IL)

( * ) Notice: Subject to any disclaimer, the term of this patent is extended or adjusted under 35 U.S.C. 154(b) by 743 days.

(21) Appl. No.: 17/051,998

(22) PCT Filed: May 1, 2019

(86) PCT No.: PCT/IB2019/000507
§ 371 (c)(1),
(2) Date: Oct. 30, 2020

(87) PCT Pub. No.: WO2019/211666
PCT Pub. Date: Nov. 7, 2019

(65) Prior Publication Data
US 2021/0242392 A1    Aug. 5, 2021

Related U.S. Application Data

(60) Provisional application No. 62/665,972, filed on May 2, 2018.

(51) Int. Cl.
*H01L 41/053* (2006.01)
*H10N 30/88* (2023.01)
(Continued)

(52) U.S. Cl.
CPC ........... *H10N 30/886* (2023.02); *B29C 55/02* (2013.01); *B29C 65/48* (2013.01); *B29C 66/022* (2013.01); *B29C 66/45* (2013.01);
*B32B 7/12* (2013.01); *B32B 27/08* (2013.01); *B32B 37/12* (2013.01); *B32B 37/182* (2013.01);
(Continued)

(58) Field of Classification Search
CPC .... H10N 30/886; H10N 30/802; H10N 30/87; H10N 30/857
See application file for complete search history.

(56) References Cited

U.S. PATENT DOCUMENTS 6,545,384 B1 * 4/2003 Pelrine .................... F02G 1/043
977/788
7,223,867 B2 * 5/2007 Palombi .................. A61P 19/02
546/205
(Continued)

FOREIGN PATENT DOCUMENTS

WO    2019/025854 A2    2/2019

OTHER PUBLICATIONS

International Search Report and Written Opinion from International Application No. PCT/IB2019/000507 dated Oct. 29, 2019.

*Primary Examiner* — Bryan P Gordon
(74) *Attorney, Agent, or Firm* — GREENBERG TRAURIG, LLP

(57) ABSTRACT

A structure including an electro-active-polymer ("EAP"). The structure can take the form of a strap, which includes two or more EAP film layers. The structure can further include one or more holders or end-grabbing portions. Methods of making and using the EAP structure are also envisioned.

20 Claims, 6 Drawing Sheets

(51) Int. Cl.
    *B29C 55/02* (2006.01)
    *B29C 65/48* (2006.01)
    *B29C 65/00* (2006.01)
    *B32B 7/12* (2006.01)
    *B32B 27/08* (2006.01)
    *B32B 37/12* (2006.01)
    *B32B 37/18* (2006.01)
    *B32B 38/00* (2006.01)
    *H10N 30/06* (2023.01)
    *H10N 30/87* (2023.01)
    *H10N 30/098* (2023.01)
    *H10N 30/80* (2023.01)
    *H10N 30/857* (2023.01)
    *B29L 31/34* (2006.01)

(52) U.S. Cl.
    CPC ......... *B32B 38/0012* (2013.01); *H10N 30/06* (2023.02); *H10N 30/098* (2023.02); *H10N 30/802* (2023.02); *H10N 30/857* (2023.02); *H10N 30/87* (2023.02); *B29K 2995/0005* (2013.01); *B29K 2995/0046* (2013.01); *B29L 2031/3406* (2013.01); *B32B 2038/0028* (2013.01); *B32B 2255/10* (2013.01); *B32B 2255/20* (2013.01); *B32B 2255/205* (2013.01); *B32B 2255/26* (2013.01); *B32B 2307/202* (2013.01); *B32B 2307/51* (2013.01); *B32B 2457/00* (2013.01)

(56) References Cited

U.S. PATENT DOCUMENTS

| | | |
|---|---|---|
| 2005/0040733 A1 | 2/2005 | Goldenberg et al. |
| 2008/0195018 A1 | 8/2008 | Larson et al. |
| 2013/0176628 A1* | 7/2013 | Batchko ............ G02B 3/12 359/665 |
| 2016/0131275 A1* | 5/2016 | Rodegheri ........ H10N 30/206 29/25.35 |
| 2016/0184141 A1* | 6/2016 | Zelka ............... H10N 30/04 29/846 |
| 2018/0198053 A1* | 7/2018 | Doyle ............ H10N 30/857 |

* cited by examiner

STRAP HAVING A PORTION OF ELECTRO-ACTIVE POLYMER, METHODS AND MECHANISMS FOR MAKING AND USING THE SAME

RELATED APPLICATIONS

This application claims the priority of U.S. provisional patent application No. 62/665,972, filed May 2, 2018; entitled "METHODS AND MECHANISMS FOR MAKING A STRAP HAVING A PORTION MADE WITH ELECTRO-ACTIVE POLYMER," which is incorporated herein by reference in its entirety.

FIELD

The field of the present disclosure pertains to electro-active polymer ("EAP") technology.

BACKGROUND

Electro-active polymers may exhibit a change in size or shape when stimulated by an electric field. There is a need for further applications of electro-active polymer technology.

SUMMARY

Some embodiments of the present disclosure relate to an apparatus comprising: at least one composite film layer. In some embodiments, each of the at least one composite film layer comprises: a pre-stretched electro-active polymer ("EAP") sublayer; and a stretchable conductive sublayer disposed on the pre-stretched EAP sublayer.

In some embodiments, the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state. In some embodiments, the stretchable conductive sublayer is configured to receive and distribute electrical current through the pre-stretched EAP sublayer while the pre-stretched EAP sublayer is maintained in the pre-stretched state.

In some embodiments, the apparatus comprises a plurality of first holders. In some embodiments, the plurality of first holders is positioned longitudinally relative to the at least one composite film layer, so that the plurality of first holders is attached on top at least one composite film layer. In some embodiments, the holders are attached by adhesion, or any other means of attachment.

In some embodiments, the apparatus comprises a plurality of second holders. In some embodiments, the plurality of second holders is positioned latitudinally relative to each of the at least one composite film layer, so that the plurality of second holders is attached on top at least one composite film layer. In some embodiments, the holders are attached by one or more adhesives, or by one or more other attachment mechanisms such as one or more welds, one or more laser bonds, one or more pressure seals, one or more heat seals, or any combination of the foregoing.

In some embodiments, the plurality of first holders is disposed orthogonally relative to the plurality of second holders to define sections of a skeleton. In some embodiments, the skeleton is configured to maintain the pre-stretched EAP sublayer in the pre-stretched state, while allowing the sublayer to expand in one or two directions.

In some embodiments, the apparatus comprises at least one end grabbing portion. In some embodiments, the at least one end grabbing portion is disposed on a longitudinal end the at least one composite film layer.

In some embodiments, the stretchable conductive sublayer is in the form of a predetermined pattern. In some embodiments, the predetermined pattern comprises a series of latitudinally oriented sections. In some embodiments, the predetermined pattern comprises a plurality of longitudinal portions. In some embodiments, each longitudinal portion of the plurality of longitudinal portions connects each latitudinally oriented section of the series of latitudinally oriented sections to an adjacent latitudinally oriented section of the series of latitudinally oriented sections. In some embodiments, each longitudinal portion of the plurality of longitudinal portions is integral with each latitudinally oriented section of the series of latitudinally oriented sections. In some embodiments, each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections.

In some embodiments, the apparatus comprises two end grabbing portions disposed on opposed longitudinal ends of the apparatus.

In some embodiments, the apparatus comprises at least one extension portion integral to at least one of the least two composite film layers, wherein the at least one extension portion is configured to allow an electrical connection to an external power source.

In some embodiments, the apparatus comprises at least one electrically insulating layer, wherein the at least one electrically insulating layer is disposed on an outer surface of each of the at least one composite film layer.

In some embodiments, the pre-stretched EAP sublayer is defined by an expansion in at least one of a latitudinal or a longitudinal direction, of from 1% to 5000% relative to an un-stretched EAP sublayer. In some embodiments, each of the at least one composite film layer are defined by an expansion in at least one of a latitudinal or a longitudinal direction, of from 1% to 5000% relative to at least two un-stretched composite film layers.

In some embodiments, the sufficiently flexible material of the stretchable conductive sublayer comprises at least one material chosen from: 1) a solution comprising: carbon or silver based conducting ink, Polyaniline (PAni), carbon, graphite powder, or any combination thereof; 2) carbon black powder, 3) conductive polymer, 4) conductive rubber, 5) conductive silver or carbon paste, 6) conductive epoxy, 7) conducting grease, 8) a laser cut or molded rigid conductive sheet in an expanding pattern, 9) a stretchable conductive sheet comprising networks of gold nano-particles, carbon nano-particles, or combinations thereof embedded in elastic polyurethane; or 10) any combination of the foregoing.

Some embodiments of the present disclosure relate to a method comprising a step of obtaining an apparatus comprising: at least one composite film layer. In some embodiments, each of the at least one composite film layer comprises: a stretchable conductive sublayer disposed on the pre-stretched EAP sublayer. In some embodiments, the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state. In some embodiments, the stretchable conductive sublayer is configured to receive and distribute electrical current through the pre-stretched EAP sublayer while the pre-stretched EAP sublayer is maintained in the pre-stretched state. In some embodiments, the apparatus comprises a plurality of first holders. In some embodiments, the plurality of first holders is positioned longitudinally relative to the at least one composite film layer, so that the plurality of first holders is attached on top at least one composite film layer. In some embodiments, the apparatus comprises a plurality of second holders. In some embodiments, the plurality of second holders is positioned latitudinally relative to the at least one composite film layer, so that the plurality of second holders is attach on top at least one composite film layer. In some embodiments, the holders are attached by adhesion, or any other means of attachment. In some embodiments, the plurality of first holders is disposed orthogonally relative to the plurality of second holders to define sections of a skeleton. In some embodiments, the skeleton is configured to maintain the pre-stretched EAP sublayer in the pre-stretched state, while allowing the sublayer to expand in one or two directions. In some embodiments, the apparatus comprises at least one end grabbing portion. In some embodiments, the at least one end grabbing portion is disposed on a longitudinal end of at least one of the at least one composite film layer.

In some embodiments, the method comprises steps of: sending, with a controller, an electrical signal and a baseline voltage to a driver circuit; transforming, with the driver circuit, the baseline voltage into a sufficient voltage to at least partially electrically activate the composite film layer, and applying the at least partial activation voltage to the at least one composite film layer, thereby at least partially electrically activating the EAP sublayer.

In some embodiments, the method comprises a step of: sending, with a controller, an electrical signal and a baseline voltage to a driver circuit. In some embodiments, the driver circuit is configured to measure a state of the pre-stretched EAP and transmit the state back to the controller. In some embodiments, the state of the pre-stretched EAP comprises at least one of: latitudinal expansion, longitudinal expansion, stretch, load, or functionality.

In some embodiments, the method comprises a step of: transforming, with the driver circuit, the baseline voltage into a sufficient voltage to at least partially electrically activate the composite film layer to at least a partial activation voltage. In some embodiments, the method comprises a step of at least partially activating the composite film layer to an activation voltage. In some embodiments, the activation voltage ranges from 10V to 20,000V.

In some embodiments, the method further includes steps of: wrapping the apparatus around a solid body; at least partially electrically activating the composite film layer to apply a first voltage to the composite film layer wherein the application of the first voltage to the composite film layer applies a first pressure to the solid body, wherein the first pressure ranges from 6 mmHg to 1000 mmHg.

In some embodiments, the method further includes a step of: applying a plurality of different voltages to the composite film layer; wherein the application of each different voltage to the at least one composite film layer applies an additional pressure to the solid body, wherein each additional pressure is different from the first pressure.

In some embodiments, the solid body is a solid body of variable stiffness. In some embodiments, the method further includes a step of: applying a plurality of different voltages to the at least one composite film layer, wherein the application of each different voltage to the solid body applies a pressure to the solid body that is the same as the first pressure, so as to compensate for the variable stiffness of the solid body.

In some embodiments, the step of "at least partially electrically activating the composite film layer to apply a first voltage to the at least one composite layer," occurs before the step of "wrapping the apparatus around a solid body," and the method further comprising a step of decreasing the voltage to a second voltage below the first voltage, so as to increase the pressure to a second pressure above the first pressure.

Some embodiments of the present disclosure are directed to a method comprising a step of mechanically stretching an electro-active polymer ("EAP") to form a pre-stretched EAP sublayer.

In some embodiments, the method comprises a step of applying, to the pre-stretched EAP sublayer, a solution comprising a flexible conductive material, thereby forming a stretchable conductive sublayer. In some embodiments, during the step of "mechanically stretching the electro-active polymer to form a pre-stretched EAP sublayer," the EAP is stretched from 1% to 5000% in at least one of a latitudinal or longitudinal direction.

In some embodiments, the method comprises a step of applying an adhesive solution to the stretchable conductive sublayer. In some embodiments, the method comprises a step of: with the adhesive solution, adhering the stretchable conductive sublayer to the pre-stretched EAP sublayer to form a composite film layer. In some embodiments, the above steps are repeated at least one time, thereby forming at least one composite film layer. In some embodiments, during the step of "applying, to the pre-stretched EAP sublayer, a solution comprising a flexible conductive material," the solution comprising the flexible conductive material is deposited onto the pre-stretched EAP sublayer according to a predetermined mask pattern, so that a shape of the stretchable conductive sublayer conforms to a shape of the predetermined mask pattern, wherein the predetermined mask pattern comprises: a series of latitudinally oriented sections and a plurality of longitudinal portions. In some embodiments, each longitudinal portion of the plurality of longitudinal portions connects each latitudinally oriented section of the series of latitudinally oriented sections to an adjacent latitudinally oriented section of the series of latitudinally oriented sections. In some embodiments, each longitudinal portion of the plurality of longitudinal portions is integral with each latitudinally oriented section of the series of latitudinally oriented sections. In some embodiments, each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections. In some embodiments, a shape of the EAP sublayer conforms to a shape of the predetermined mask pattern. In some embodiments, during the step of "applying an adhesive solution to the stretchable conductive sublayer," the solution comprising the adhesive solution is deposited onto the stretchable conductive sublayer according to the predetermined mask pattern.

In some embodiments, the method comprises a step of: attaching a plurality of first holders on top the at least one composite film layer. In some embodiments, the method comprises a step of: positioning the plurality of first holders longitudinally relative to the at least one composite film layer. In some embodiments, the method comprises a step of: attaching a plurality of second holders on top the at least one composite film layer.

In some embodiments, the method comprises a step of: positioning the plurality of second holders latitudinally relative to the at least one composite film layer and orthogonally relative to the plurality of second holders to define sections of a skeleton and thereby maintain the pre-stretched EAP sublayer in the pre-stretched state, while allowing the sublayer to expand in one or two directions.

In some embodiments, the method comprises a step of: disposing at least one end grabbing portion on a longitudinal end of at least one of the at least one composite film layer.

In some embodiments, the method comprises a step of applying an electrically insulating layer to at least one surface of at least one composite film layer.

In some embodiments, the method comprises a step of attaching to the EAP structure, at least one of: an extension configured to allow an electrical connection to an external power source, a driver circuit, a controller, a processor, or a signal generator.

BRIEF DESCRIPTION OF THE DRAWINGS

The figures constitute a part of this specification and include illustrative embodiments of the present invention and illustrate various objects and features thereof. Further, the figures are not necessarily to scale, some features may be exaggerated to show details of particular components. In addition, any measurements, specifications and the like shown in the figures are intended to be illustrative, and not restrictive. Therefore, specific structural and functional details disclosed herein are not to be interpreted as limiting, but merely as a representative basis for teaching one skilled in the art to variously employ the present invention.

DETAILED DESCRIPTION

Figure 1:
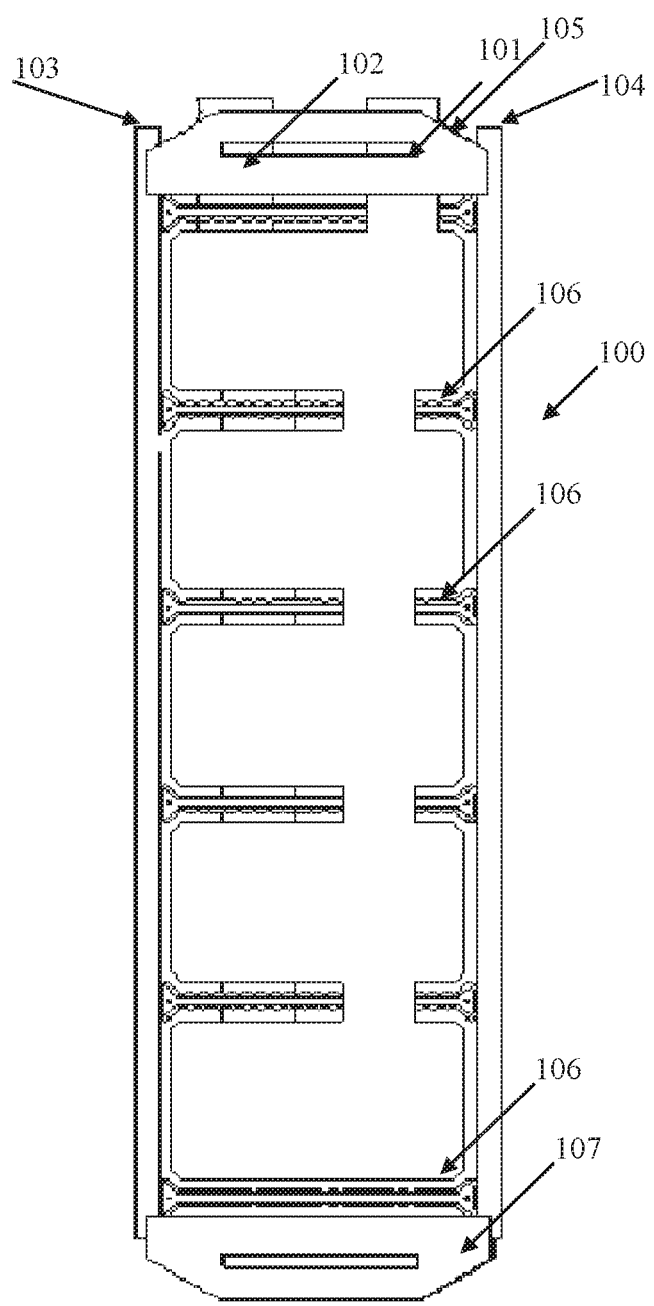
FIG. 1 shows an exemplary electro-active-polymer structure according to the present disclosure.

Reference will now be made to several embodiments of the present disclosure(s), examples of which are illustrated in the accompanying figures. Wherever practicable similar or like reference numbers may be used in the figures and may indicate similar or like functionality. The figures depict embodiments of the present disclosure for purposes of illustration only. One skilled in the art will readily recognize from the following description that alternative embodiments of the structures and methods illustrated herein may be employed without departing from the principles of the disclosure described herein. The terms, "for example", "e.g.", "optionally", as used herein, are intended to be used to introduce non-limiting examples.

The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments of the disclosure may be readily combined, without departing from the scope or spirit of the disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

Throughout this description the term "Electro-Active Polymer," "electro-active polymer" or "EAP" is used to indicate dielectric elastomer film(s) adapted to be stretched biaxially or in a single axis. The use of the term "EAP" is a general descriptive of a genus and should not be limited to any particular shape, construction material and/or geometry, and at least some embodiments of the present disclosure are directed to all suitable elastic materials, such as the 3M™ VHB™ 4910, 4905, 4955, 4959 or 9460 Tape, the Hi-Bond VST4050 Tape, Dow Corning™ or Nusil™ silicon elastomer, Elastosil or Silpuran film by Wacker, ePTFE or any other suitable silicon, acrylic, PTFE, rubber, parylene or polyacrylamide dielectric elastomer.

As used herein, a "conductor" refers to an object or type of material that allows the flow of electrical current in one or more directions.

As used herein the terms "stretchable conductive sublayer," "stretchable conductive coating," and "stretchable conductor," can refer to a material, that when present on a pre-stretched EAP (e.g., as a coating), has a structure that is sufficiently flexible to maintain the EAP in its pre-stretched state when not acted on by an external force. The terms "stretchable conductive sublayer," "stretchable conductive coating," and "stretchable conductor," can also refer to a material that has a structure that is sufficiently conductive such that when the material is present on a pre-stretched EAP (e.g., as a coating), the material allows the EAP to remain dielectric even when the EAP is acted on by an external force (e.g., a force provided by an electrical current), such that the EAP is expanded or compressed beyond the pre-stretched state.

As used herein, the term "activation voltage," is defined as the voltage corresponding to a desired maximum stretch of the "pre-stretched" EAP. The desired maximum stretch can be determined based on at least one suitable characteristic chosen from: EAP material type, EAP material thickness, EAP strap thickness, the desired use of the EAP material (e.g., a particular medical condition), the type of solid body, the type of stretchable conductor, the thickness of a stretchable conductive layer, the like, or any combination thereof. As used herein, the term "partial activation voltage," is defined as any voltage less than the "activation voltage," but greater than the minimum voltage required for the EAP to be in a "pre-stretched" state (i.e., a baseline voltage, e.g., 10V as described in some embodiments herein).

In some embodiments, manually pre-stretching the electro-active polymer film, can be accomplished by pulling the film. In some embodiments, the EAP film might be held by clips at its edges. In some embodiments, pulling the EAP film might be performed by pulling one of the clips. In some embodiments, limiting the motion of the clip by using a barrier, limits the pre-stretch of the EAP film by a predetermined amount. In some embodiments, an example of such barrier, is a sleeve with sewn edges e.g. placing an EAP film in the sleeve and limiting the movement of the clip by a sewn edge. In some embodiment, fixing the clips in place, holds the EAP film in a pre-determined pre-stretched state. In some embodiments, fixing the clips in place is made by wrapping the EAP film around a solid body, and connecting one clip to a second clip.

In some embodiments, the solid body is a human or animal body part. In some embodiment, connecting the clips is made by a mechanical connector, for example but not limited to: Velcro, buckle, lock or any other type of mechanical connector. In some embodiments the sleeve might be made of fabric or any other material.

In some embodiments, wrapping the EAP film around solid body, applies sufficient pressure to the solid body. In some embodiments, at least partially activating the EAP film reduces the pressure which is applied on the solid body by sufficiently relaxing the EAP film. In some embodiments, at least partially deactivating the EAP film, raises the pressure which is applied on the solid body by stretching the EAP film. In some embodiments, the inventive EAP film of the present disclosure can take the form of a compression device. In some embodiments, X number of EAP films can wrapped around the solid body, wherein X is ranges from 2 and 10,000. In some embodiment, the EAP films can be wrapped in parallel along the solid body. In some embodiment, at least partially activating the EAP films simultaneously can be used to apply intermittent compression. In some embodiments, at least partially activating the EAP films sequentially can be used to apply intermittent sequential compression. In some embodiments, X is the time required to raise or reduce the pressure applied by an EAP film, by at least partially deactivating or activating the EAP film, wherein X ranges from 0.01 seconds and 100 seconds. In some embodiments, when applying intermittent compression using the EAP film, the pressure is kept sufficient for X amount of time, wherein X ranges from 0.01 seconds and 1 hour. In some embodiments, when applying intermittent compression using the EAP film, the pressure is kept low for X amount of time, wherein X ranges from 0.01 seconds and 1 hour. In some embodiments, when applying sequential compression using the EAP film, the pressure is kept high for X amount of time, wherein X ranges from 0.01 seconds and 1 hour. In some embodiments, when applying sequential compression using the EAP film, the pressure is kept low for X amount of time, wherein X ranges from 0.01 seconds and 1 hour. In some embodiments, when applying sequential compression, the time difference ranges from at least partially activating on EAP film and a different EAP film is X, wherein X ranges from 0.01 seconds and 100 seconds.

In some embodiments, the method further includes steps of: wrapping the apparatus around a solid body and at least partially electrically activating the conductive film layer to apply a first voltage to the EAP sublayer, wherein the application of the first voltage to the solid body applies or reduces a first pressure to the solid body.

In some embodiments, the present disclosure provides a method for keeping the electro-active polymer film in a pre-stretched state/condition on a single axis, by wrapping and fixing it around a solid body, e.g. a human body part.

In some embodiments, the EAP is either ON or OFF (activated or deactivated). In some embodiments, the EAP is partially activated. In some embodiments, pressure can be varied by a certain amount by changing the voltage, so that different treatment options can be applied for different patients.

In some embodiments, varying the voltage can keep a constant pressure on a solid body. For example, if a stiffness of the solid body is variable, (e.g. because the solid body is bent or straightened) the voltage can be varied to account for this change.

In some embodiments, a voltage is applied to the EAP while at least partially activated to make the voltage easier to apply, such that after the voltage is applied, the strap can be at least partially deactivated to increase an applied pressure.

In some embodiments, the EAP film is applying high pressure, such that the pressure ranges from 6 mmHg and 1000 mmHg. In some embodiments, such that the EAP film is applying low pressure, the pressure ranges from 5 mmHg and 999 mmHg.

In some embodiments, the solid body is a solid body of variable stiffness. In some embodiments, the method further includes a step of: applying a plurality of different voltages to the solid body, wherein the application of each different voltage to the solid body applies a pressure to the solid body, wherein each additional pressure is the same as the first pressure, so as to compensate for the variable stiffness of the solid body (e.g, a human arm or leg).

In some embodiments, the step of "at least partially electrically activating the EAP sublayer to apply a first voltage to the EAP sublayer," occurs before the step of "wrapping the apparatus around a solid body," the method further comprising a step of decreasing the voltage to a second voltage below the first voltage, so as to increase the pressure to a second pressure above the first pressure.

In some embodiments, the EAP film is coated by a stretchable conductor. In some embodiments, the exemplary stretchable conductor utilized in accordance with the present disclosure can be created by a conducting polymer or any other suitable stretchable conductor.

In some embodiments, said conductor might be a stretchable conductor formed by and/or comprising: 1) a conductor-built solution that may be, for example but not limited by, carbon or silver based conducting ink, Polyaniline (PAni) based solution, carbon based solution, graphite powder based solution; 2) carbon black powder, 3) conducting polymer, 4) conductive rubber, 5) conductive silver or carbon paste, 6) conductive epoxy, 7) conducting grease, 8) laser cut or molded rigid conducting sheet in an expanding pattern, 9) stretchable conducting sheet made by networks of gold and/or carbon nano-particles embedded in elastic polyurethane; or any combination thereof. In some embodiment, said conductor might be attached to the EAP film by, for example but not limited to, printing, etching, brushing, water dispersion, gluing and/or any other similarly suitable method(s) of attachment or any combination thereof. In some embodiments, the stretchable conductor is made from carbon black powder. In some embodiments, the stretchable conductor is made from a conductive polymer. In some embodiments, the stretchable conductor is made from conductive rubber. In some embodiments, the expanding pattern is one of a zigzag pattern, and expanding diamond pattern. In some embodiments, an exemplary conductor is in a form of a semi-stiff conductor made, for example but not limited to, by a conducting ink (e.g., silver and/or carbon based conductive ink, such as, but not limited to, 125-10 silver based electrically conductive ink or 112-48 carbon based conductive ink manufactured by Creative Materials, Inc. In some embodiments, the exemplary conductor is in a form of a stretchable conductor, such as, for example, a stretchable electrical conductor that is created out of networks of gold and/or carbon nano-particles embedded in elastic polyurethane. In some embodiments, the exemplary conductor is made from a carbon black powder layer attached to the electro-active polymer, for example but not limited to, Ketjenblack EC-600JD powder by Akzo Nobel (Amsterdam, Netherlands), Super C 65 by C-Nergy or 250P by Ensaco (Timcal, Cleveland, OH). In some embodiments, the exemplary conductor is made from carbon or silver paste, for example but not limited to WIK20489-56A by Henkel (Düsseldorf, Germany). In some embodiments, the exemplary conductor is made from carbon or silver conductive epoxy, for example but not limited to H20E by Epo-Teck. In some embodiments, the exemplary conductor is made by Polyaniline (PAni) based solution, carbon based solution, a laser cut or molded rigid conducting sheet, or any combination thereof.

The term "pre-stretch," and its variants are being used herein to describe mechanically stretching of an electro-active polymer film in a single axis or biaxial planar direction, such as in latitudinal and/or longitudinal directions, prior to at least partial activation. In some embodiments, by maintaining the EAP in the pre-stretch state/condition, the EAP can exhibit:
  i) increased electrical breakdown strength,
  ii) minimized or eliminated pull-in instability; and/or
  iii) decreased thickness;
  iv) lowered required voltage for at least partial activation of the EAP.

In some embodiments, the term "pre-stretch" refers to any mechanical stretch from 1%-5000% of the electro-active polymer film original size. In some embodiments, the "pre-stretch" refers to any mechanical stretch from 1%-100% of the electro-active polymer film original size. In some embodiments, the term "pre-stretch" refers to any mechanical stretch from 50%-100% of the electro-active polymer film original size. In some embodiments, the term "pre-stretch" refers to any mechanical stretch from 50%-1000% of the electro-active polymer film original size. In some embodiments, the term "pre-stretch" refers to any mechanical stretch from 100%-5000% of the electro-active polymer film original size. In some embodiments, the term "pre-stretch" refers to any mechanical stretch from 1000%-5000% of the electro-active polymer film original size. In some embodiments, the term "pre-stretch" refers to any mechanical stretch from 2500%-5000% of the electro-active polymer film original size.

In some embodiments, the exemplary method of the present disclosure further includes using more than one layer and up to 1,000 layers of electro-active polymer films in order to improve strength and/or durability of the EAP film. In some embodiments, the exemplary method of the present disclosure further includes using more than one layer and up to 100 layers of electro-active polymer films in order to improve strength and/or durability of the EAP film.

FIG. 1 shows an illustrative embodiment (100) in the form of a strap of that is constructed in accordance of one or more principles of the present disclosure. FIG. 1 shows that the illustrative embodiment of the strap (100) may include at least two EAP film-conductor layers (101, 102). In some embodiments, each layer of the at least two EAP film-conductor layers (101, 102) can be shaped in accordance with at least one pre-determined pattern and include at least one sublayer of the pre-stretched EAP film and at least one sublayer of stretchable conductor. FIG. 1 shows that the illustrative embodiment of the strap (100) may further include:
  i) two side holders (103, 104);
  ii) a first end grabbing mechanism 105;
  iii) a second end grabbing mechanism 107; and
  iv) one or more holders (106).

Figure 2:
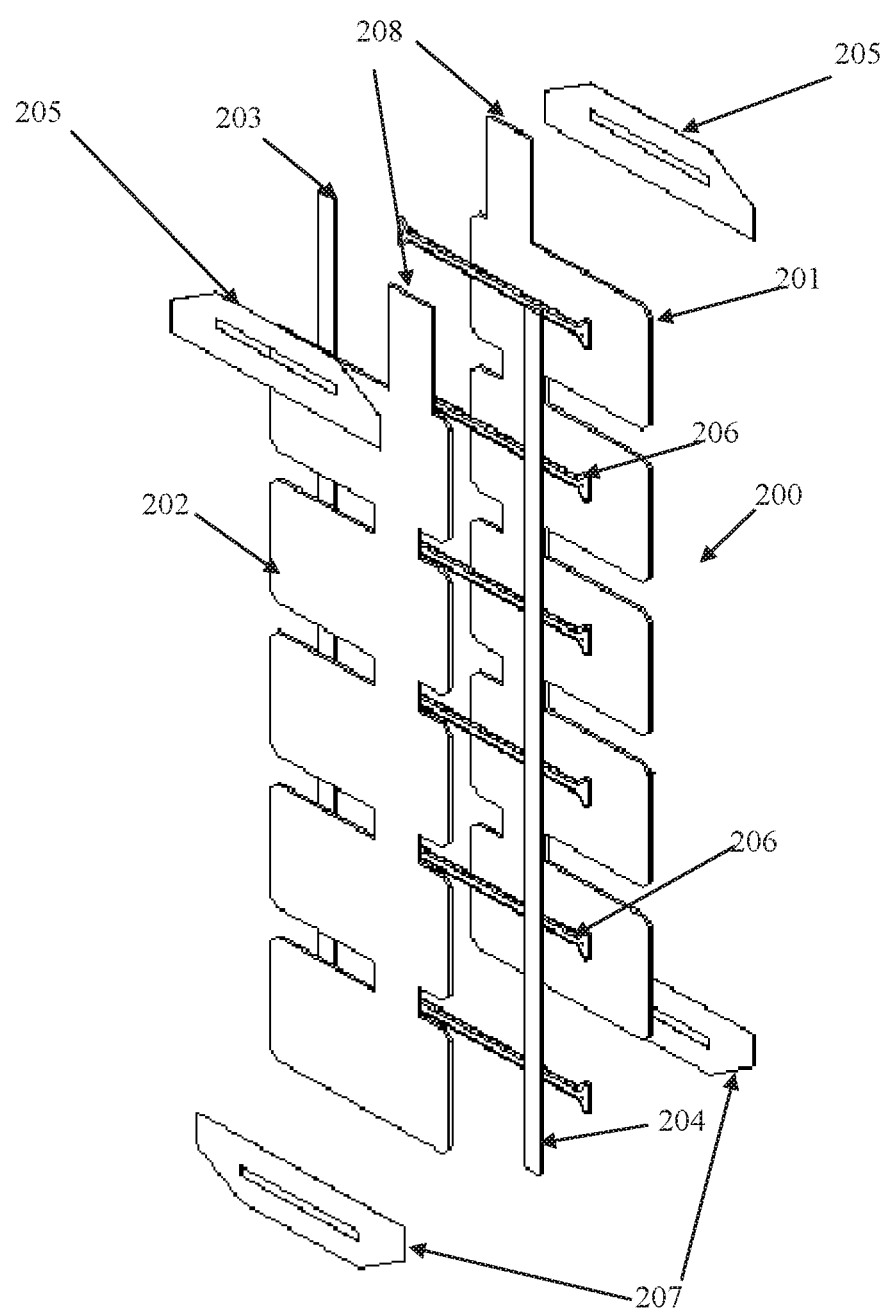
FIG. 2 shows a further exemplary electro-active-polymer structure according to the present disclosure.

FIG. 2 shows an exploded view of another illustrative embodiment (200) of a structure in accordance with at least some principles of the present disclosure. FIG. 2 shows that the illustrative embodiment (200) may include at least two EAP film-conductor layers (201, 202). In some embodiments, each layer of the at least two EAP film-conductor layers (201, 202) can be shaped in accordance with at least one pre-determined pattern and include at least one sublayer of the pre-stretched EAP film and at least one sublayer of stretchable conductor. In some embodiments, at an edge of each EAP film-conductor layer (201,202), an extension (208) can be made to allow an electrical connection to an external power source. In some embodiments, the extension (208) is integral with each EAP film conductor layer (201, 202). FIG. 2 shows that the illustrative embodiment (200) may further include:
  i) two side holders (203, 204);
  ii) a plurality of first end grabbing mechanisms 205;
  iii) a plurality of second end grabbing mechanisms 207; and
  iv) one or more holders (206).

Figure 5:
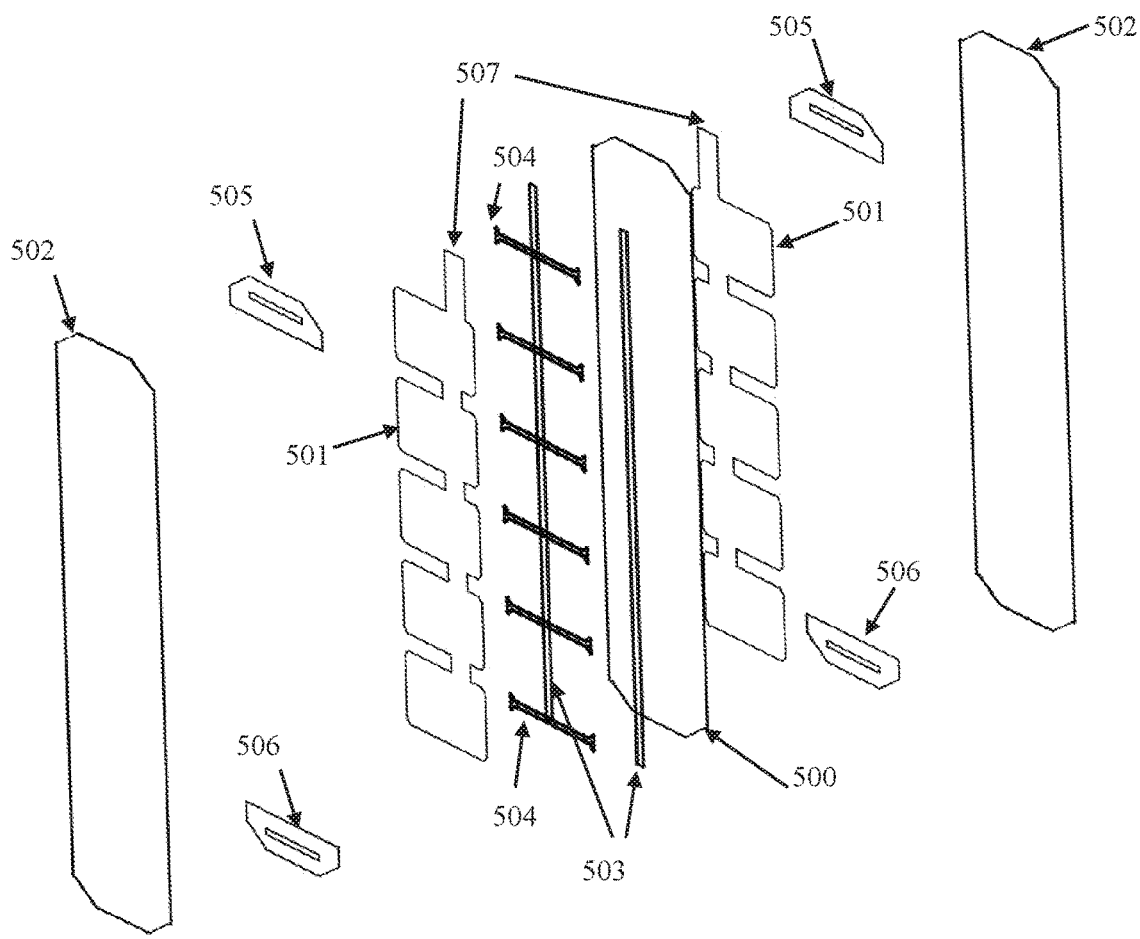
FIG. 5 shows an exploded view of a further exemplary electro-active-polymer structure according to the present disclosure.

FIG. 5 shows an exploded view of another illustrative embodiment (500) of a structure made in accordance with at least some principles of the present disclosure. FIG. 5 shows that the illustrative embodiment (500) may include at least two EAP film-conductor layers (501). In some embodiments, each layer of the at least two EAP film-conductor layers (501) can be shaped in accordance with at least one pre-determined pattern and include at least one sublayer of the pre-stretched EAP film and at least one sublayer of stretchable conductor. In some embodiments, an edge of each EAP film-conductor layers (501), such as a longitudinal edge, an extension can be made (507) to allow an electrical connection to an external power source. FIG. 5 shows that the illustrative embodiment (500) may further include:
  i) two side holders (503);
  ii) electrically insulating layer (502);
  Iii) a plurality of first end grabbing mechanisms 505;
  iv) a plurality of second end grabbing mechanisms 506; and
  v) one or more holders (504).

Figure 6:
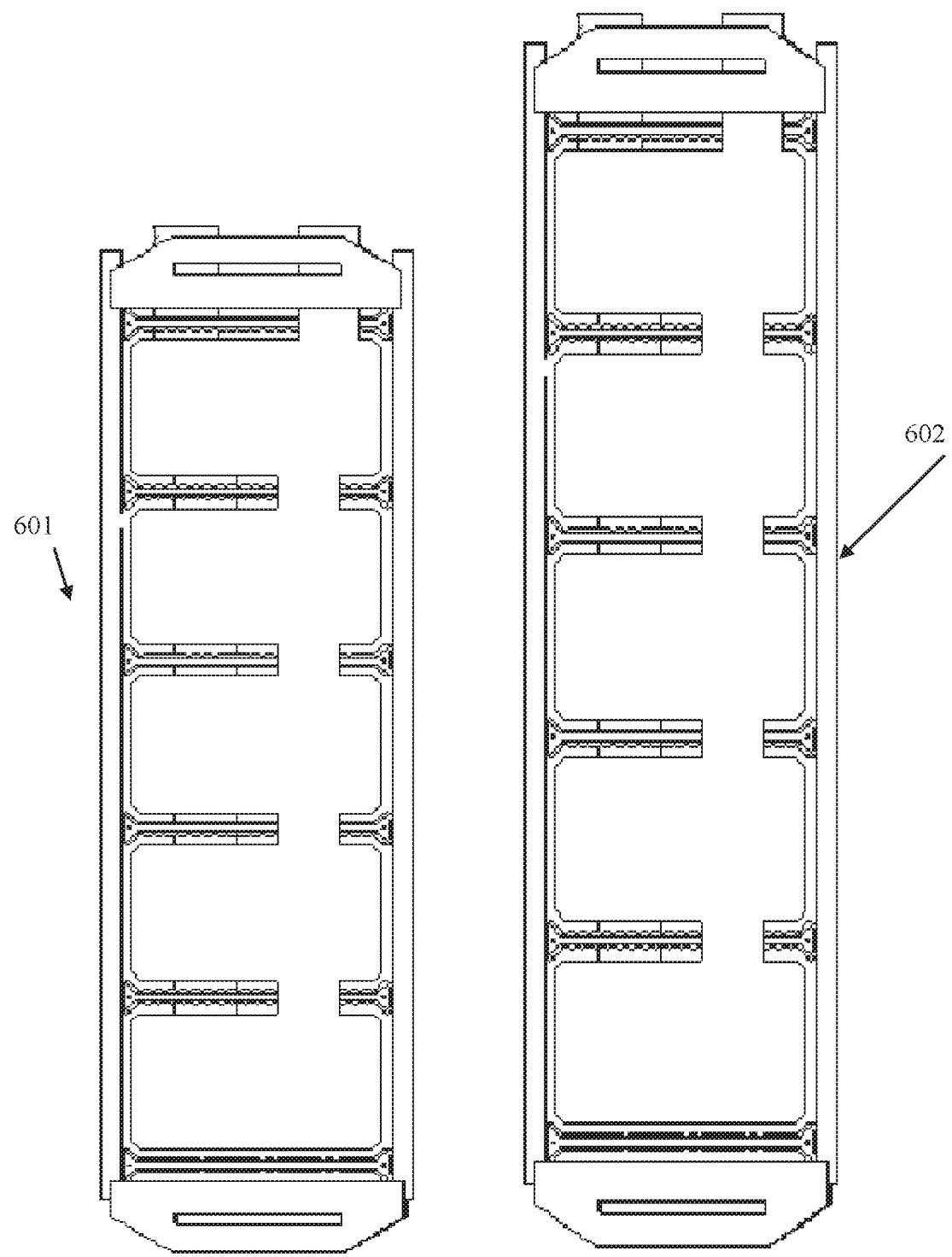
FIG. 6 shows a further electro-active-polymer structure according to the present disclosure.

FIG. 6 shows an illustrative embodiment (601) the inventive structure in the form of a strap. FIG. 6 shows the illustrative embodiment is expanded by X percent (602) from its original size in a single axis when at least partially electrically activated. In some embodiments X ranges from 3-1000. In some embodiments X ranges from 3-500. In some embodiments X ranges from 3-100. In some embodiments X ranges from 50-1000. In some embodiments X is ranges from 100-1000. In some embodiments X is ranges from 500-1000.

Figure 7:
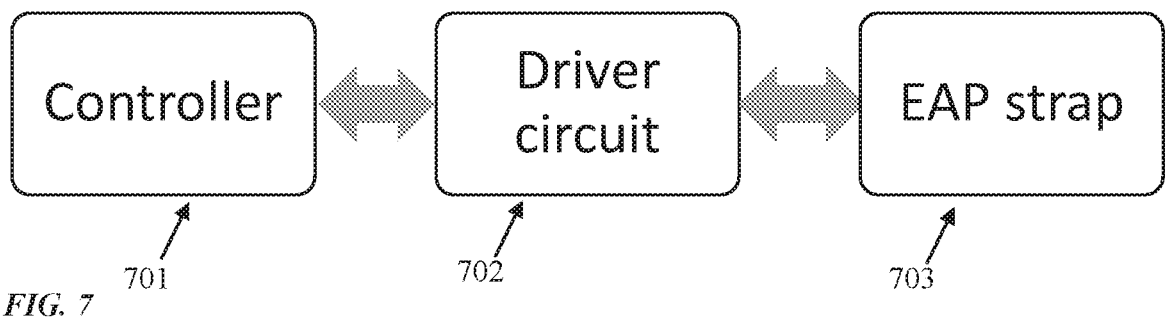
FIG. 7 shows a block diagram, generally illustrating exemplary components used for electrical activation of an electro-active-polymer structure.

FIG. 7 shows a block diagram, generally illustrating exemplary components used for the at least partial electrical activation of an EAP strap. A controller (701) can send an electrical signal and baseline voltage to a driver circuit (702). The driver circuit (702) can transform the baseline voltage into a required voltage for at least partial activation of the EAP strap (703). In some embodiments, the driver circuit (702) can be connected to the EAP strap (703) via extensions at the edge of each EAP film-conductor layer (208, 507). In some embodiments, the at least partial activation voltage is applied to the extensions at the edge of each EAP film-conductor layer (208, 507). In some embodiments, the driver circuit (702) can measure the state of the EAP strap (703), for example, but not limited to, amount of lateral and/or longitudinal expansion, stretch, load and functionality. In some embodiments, the driver circuit (702) can transmit the state of the EAP strap (703) back to the controller (701).

In some embodiments, the exemplary structure in the form of a strap may have a length X, a width Y and a thickness Z. In some embodiments, X ranges from 0.01-10000 mm. In some embodiments, X ranges from 0.1-1000 mm. In some embodiments, X ranges from 1-10000 mm. In some embodiments, X ranges from 1-1000 mm. In some embodiments, Y ranges from 0.01-10000 mm. In some embodiments, Y ranges from 0.1-1000 mm. In some embodiments, Y ranges from 1-1000 mm. In some embodiments, Y ranges from 1-1000 mm. In some embodiments, Z ranges from 0.01-1000 mm. In some embodiments, Z ranges from 0.1-1000 mm. In some embodiments, Z ranges from 1-1000 mm. In some embodiments, Z ranges from 1-1000 mm.

In some embodiments, each sublayer of the pre-stretched EAP film may have a thickness that varies from 0.5-1.0 millimeters (mm). In some embodiments, the thickness of each sublayer of the pre-stretched EAP film may range from 10 μm-5 mm. In some embodiments, the thickness of each sublayer of the pre-stretched EAP film may range from 100 μm-5 mm. In some embodiments, the thickness of each sublayer of the pre-stretched EAP film may be between 1000 um-5 mm. In some embodiments, the thickness of each sublayer of the pre-stretched EAP film may range from 10 um-1 mm. In some embodiments, the thickness of each sublayer of the pre-stretched EAP film may be from 100 um-1 mm. In some embodiments, the thickness of each sublayer of the pre-stretched EAP film may range from 500 um-1 mm.

In some embodiments, each sublayer of the stretchable conductor may be created when a conductor-built solution having, for example but not necessarily limited to, carbon black powder mixed with methanol being deposited in one or more passes over a mask (e.g., FIG. 3) having a predetermined pattern and being placed on top of the respective sublayer of the pre-stretched EAP film. In some embodiments, the deposition of the at least one conductor material may be accomplished by an air spray. In case of the exemplary conductor-built solution of carbon black powder with methanol, after the deposition, methanol would evaporate and the carbon black powder would be left attached on the top of the respective sublayer of the pre-stretched EAP film. In some embodiments, methanol may be replaced by or being combination with any other suitable solvent (e.g., ethanol, acetone, ethyl acetate, toluene, butanol, ethyl acetate).

In some embodiments, there may be an adhesive solution deposited as another sublayer on top of a respective sublayer with the stretchable conductor. In some embodiments, an exemplary adhesive solution may be a solution that includes, but not necessarily limited to, one or more adhesives mixed with suitable solvent (e.g., methanol, acetone, ethyl acetate, toluene, butanol, ethyl acetate).

For example, when methanol would evaporate, the adhesive would be left and would serve as a further adhesive mechanism to adhere the successive layers of various embodiments (e.g., 100, 200, 500) of the inventive structure of the present disclosure. In some embodiments, methanol may be replaced by or being combination with any other suitable solvent (e.g. ethanol, acetone, ethyl acetate, toluene, butanol, ethyl acetate). In some embodiments, the adhesive may be replaced by or being combination with any other suitable material that exhibits similarly suitable adhesive characteristic without adding any rigidity or adding only operatively insignificant rigidity (e.g., in one example: added rigidity is less than 15%; in another example: added rigidity is less than 10%; in yet another example: added rigidity is less than 5%; in yet another example: added rigidity is less than 1%).

In some embodiments, the exemplary conductor-built solution may also further include at least one adhesive.

Figure 4:
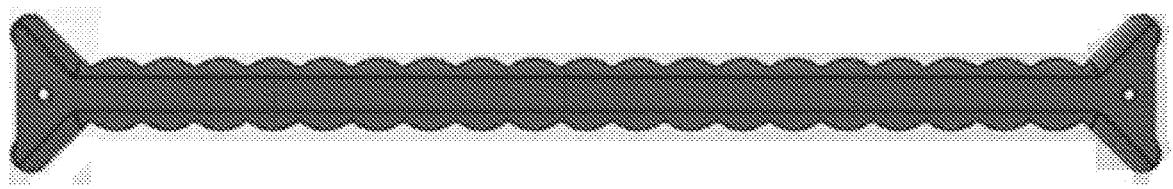
FIG. 4 shows an exemplary holder according to the present disclosure.

In some embodiments, the holders (e.g., 106, 206, 504) may be made from any suitable plastic material(s) such as, but not limited to, polycarbonate, polypropylene, polystyrene, polyethylene, polyacrylamide, polyphthalamide, glass fiber, or any other similar type material. In some embodiments, the holders (106, 206, 504) may be of any suitable shape (e.g., FIG. 4). In some embodiments, the holders (106, 206, 504) may be of any suitable thickness (e.g., 1 mm). In some embodiments, the holders (106, 206, 504) may be of any suitable length what may extend over significant portion of the width or the entire width of the respective embodiments (e.g., 100, 200, 500) of the inventive structure. In some embodiments, the holders (106, 206, 504) may be attached to respective layer(s) by various suitable methods such as, but not limited to, gluing. In some embodiments, the holders (106, 206, 504) may be placed between successive layers without any attachment method.

In some embodiments, each grabbing mechanism may have suitable size, shape and/or thickness. In some embodiments, each grabbing mechanism may vary in suitable material, size, shape and/or thickness. For example, a grabbing mechanism may have thickness of at least 0.1 mm. In some embodiments, the thickness of the exemplary grabbing mechanism may vary between 0.1 mm and 5 mm. In some embodiments, the thickness of the exemplary grabbing mechanism may vary between 1 mm and 5 mm. For example, a grabbing mechanism may be made from material(s) such as, but not limited to, polyvinyl chloride or similarly suitable material(s).

In some embodiments, each side holder (e.g., 103, 104, 203, or 204, 503) may have suitable size, shape and/or thickness. In some embodiments, each side holder may vary in suitable material, size, shape and/or thickness. For example, a side holder may have a thickness X mm and a width Y mm. In some embodiments, Y would be larger than X. In some embodiments, Y would be equal to X. In some embodiments, X is between 0.01-100 mm. In some embodiments, X is between 0.1-100 mm. In some embodiments, X is between 0.01-50 mm. In some embodiments, Y is between 0.01-100 mm. In some embodiments, Y is between 0.1-100 mm. In some embodiments, Y is between 0.01-50 mm. For example, a side holder may be made from material(s) such as, but not limited to, elastomer (e.g., the EAP film that is folded X times and cut to desired size, shape and thickness).

In some embodiments, the inventive structure (e.g., 100, 200, 500) may be formed in accordance with the following exemplary sequence of steps. At Step 1, the EAP film is mechanically stretched by a designated stretching machine to obtain the pre-stretched EAP film that is kept in the pre-stretched state throughout the assembly process to form the exemplary structure (e.g., 100, 200, 500). In some embodiments, the pre-stretched EAP film that is kept in the pre-stretched state throughout the assembly process in accordance with one or more methods detailed in U.S. Pat. No. 9,433,537 and/or WIPO Publication No. WO 2019/025854, each of which is hereby incorporated by reference herein in its respective entirety. The pre-stretched EAP film forms each respective sublayer of the pre-stretched EAP film of each respective layer.

Figure 3:
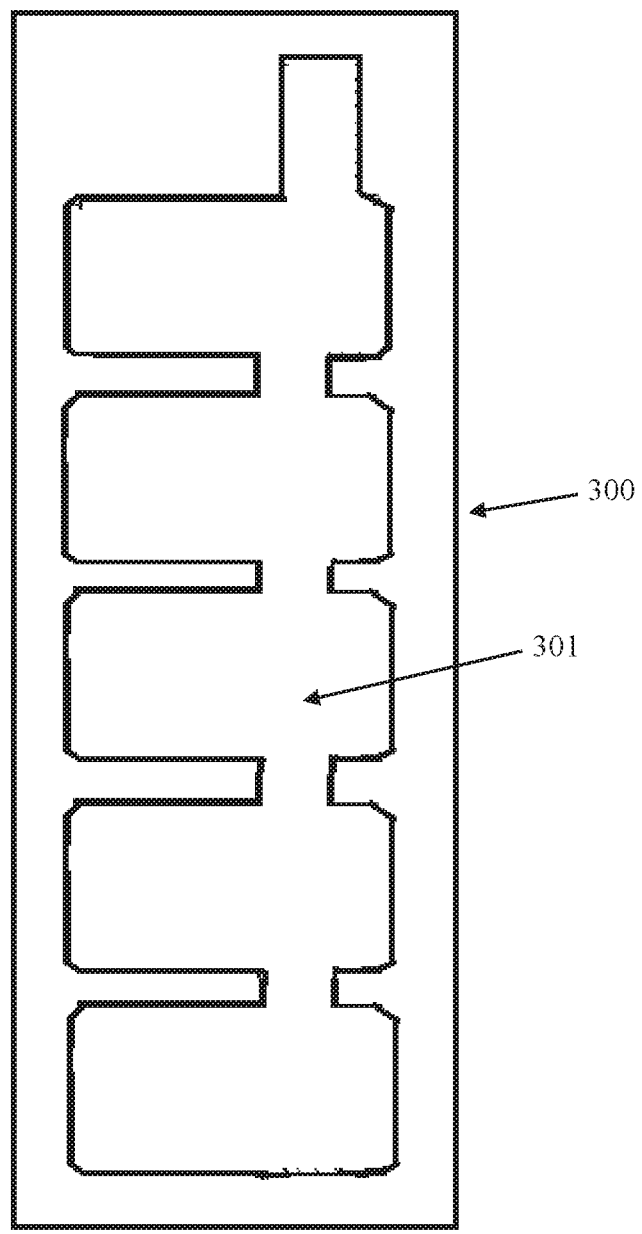
FIG. 3 shows an exemplary electro-active-polymer pattern according to the present disclosure.

At Step 2, at least one coat a solution having the exemplary stretchable conductor may be deposited onto each respective sublayer of the pre-stretched EAP film coating to form each respective sublayer of stretchable conductor of each respective layer. For example, as detailed above, the exemplary conductor-built solution can be deposited via utilizing a pre-determined mask pattern. For example, FIG. 3 shows an exemplary pre-determined mask pattern (300) having a cutout (301) of a pre-determined shape into which the exemplary conductor-built solution is deposited onto each respective sublayer of the pre-stretched EAP film coating. For example, a respective sublayer of the stretchable conductor may be from 1-100 cm wide and 1-300 cm long. For example, a respective sublayer of stretchable conductor may be from 1-60 cm wide and 1-100 cm long. For example, a respective sublayer of stretchable conductor may be from 1-10 cm wide and 10-50 cm long. For example, a respective sublayer of stretchable conductor may be from 6-10 cm wide and 20-40 cm long.

At Step 3, after forming the stretchable conductor, at least one coat of the exemplary adhesive solution is deposited on top the stretchable conductor sublayer to provide additional adhesion between the successive layers (e.g., 101 and 102, 201 and 202, 501).

At Step 4, steps 1-3 are repeated Z pre-determined times to obtain, for example, but not limited to, Z-layer structures (e.g., 100, 200, 500). In some embodiment, Z may vary from 2 and 10,000. In some embodiment, Z may be at least 2. In some embodiment, Z may be at least 10. In some embodiment, Z may be at least 100. In some embodiment, Z may be at least 1,000. In some embodiment, Z may be at least 10,000.

During Step 4, with a pre-determined, suitable periodicity, a S number of the holders (e.g., 106, 206) is placed between a pair of successive layers to create a chassis or skeleton. In some embodiments, the S number may vary from 1 to 100. For example, if the exemplary inventive structures (e.g., 100, 200, 500) is desired to have 10 EAP film-conductor layers, then a plurality of holders can be placed within 2 pairs of layers, where each pair of layers having the respective plurality of holders between them is separate, by at least one EAP film-conductor layer having no holders, from the other pair of layers having the respective plurality of holders between them.

During Step 4, a pair of side holders (e.g., 103 and 104, 203 and 204, 503) is placed between at least one pair of successive layers on each longitudinal side of the exemplary inventive structure (e.g., 100, 200, 500). In some embodiments, the pair of side holders (e.g., 103 and 104, 203 and 204, 503) may be place after at least a R number of layers have been assembled. For example, R may be equal to a rounded number of a half of Z. For example, R may be equal to a rounded number of a quarter of Z. For example, R may be equal to a rounded number of a third of Z.

During Step 4, at least one first end grabbing mechanism (e.g., 105, 205, 505) and at least one second end grabbing mechanism (e.g., 107, 207, 506) may be placed at one or more suitable positions to allow for holding the exemplary inventive structure (e.g., 100, 200, 500), such as, but not limited to, positions selected from:

1) both being between at least one pair of successive layers,
2) one being between a first pair of successive layers and the other being a second pair of successive layers,
3) one being between a pair of successive layers, the other being a layer of the pair of successive layers and another successive layer;
4) both being attached to the non-conductor side of the initial layer;
5) both being attached to the non-conductor side of the final layer;
6) any combination thereof.

In some embodiments, one or more grabbing mechanisms may be further secured at their respective position by a suitable adhesive (e.g., non-rigidity-imparting glue, etc.).

In some embodiments, after Step 4, optionally, a non-stretched elastomer film of a pre-determined thickness (not stretched) may be attached on both sides of the exemplary inventive structure (e.g., 100, 200, 500) to further support the pre-stretched state of the exemplary inventive structure.

In some embodiments, after Step 4, the exemplary inventive structure (e.g., 100, 200, 500) is mechanically separated from the rest of the EAP film. In some embodiments, after Step 4, the exemplary inventive structure (e.g., 100, 200, 500) is coated on one or both sides by an electrically insulating layer (e.g. 502). In some embodiments, the electrically insulating layer (e.g. 502) is also used to mechanically stabilize the inventive structure. In some embodiments, the electrically insulating layer (e.g. 502) is made of silicon elastomer, acrylic elastomer, rubber or any other electrically insulating material. In some embodiments, the thickness of the electrically insulating layer (e.g. 502) is from 0.01 mm to 10 cm. In some embodiments, more than one layer of electrical insulating material might be used in each side of the exemplary inventive structure. In some embodiments, the coating can be made by pouring, printing, etching, brushing, water dispersion, gluing, ion-attachment and/or any other suitable method of the attachment.

In some embodiments, at the edge of each EAP film-conductor layer (201,202), an extension can be made (208, 507) to allow an electrical connection to an external power source. In some embodiments, the extension is attached via electrical wiring to a driver circuit. In some embodiments, the driver circuit transforms an input voltage (for example, from a controller, battery or any other external power source), into the required voltage for at least partial activation. In some embodiments, the required voltage for at least partial activation is set according to an input signal, for example but not limited to from a controller, processor or any other signal generator. In some embodiments, the driver circuit is placed at the edge of the strap.

In some embodiments, the exemplary conductor utilized in accordance with the present disclosure is selected from the group consisting of a stretchable conductor, a rigid conductor in an expanding pattern, a printed conductor in an expanding pattern, and any combination thereof.

In some embodiments, the exemplary stretchable conductor utilized in accordance with the present disclosure can be created out of networks of gold and/or carbon nano-particles embedded in elastic polyurethane, or any other suitable stretchable conductor.

In some embodiments, the exemplary stretchable conductor utilized in accordance with the present disclosure can be created by a layer of carbon black powder glued to the electro-active polymer or any other suitable stretchable conductor.

In some embodiments, the exemplary stretchable conductor utilized in accordance with the present disclosure can be created by a conducting rubber or any other suitable stretchable conductor.

In some embodiments, the exemplary stretchable conductor utilized in accordance with the present disclosure can be created by applying a carbon or silver paste or any other suitable stretchable conductor.

In some embodiments, the exemplary stretchable conductor utilized in accordance with the present disclosure can be created by applying a carbon or silver epoxy or any other suitable stretchable conductor.

In some embodiments, the exemplary printed conductor utilized in accordance with the present can be a made utilizing a conducting ink based on silver and/or carbon.

In some embodiments, the attachment of an exemplary conductor to an electro-active polymer is done by printing, etching, brushing, water dispersion, gluing, ion-attachment and/or any other suitable method of the attachment.

In some embodiments, an exemplary EAP film can be at least partially activated by applying an electric charge on the conducting layers attached to the electro-active polymer film, thus creating an electric field which expands the electro-active polymer film in a single axis or biaxial direction. In some embodiments, the at least partial activation creates an expansion of the exemplary EAP film by 3%-100% in a single axis or biaxial directions from its original size. In some embodiments, the at least partial activation creates an expansion of the exemplary EAP film by 3%-500% in a single axis or biaxial directions from its original size. In some embodiments, the at least partial activation creates an expansion of the exemplary EAP film by 3%-1000% in a single axis or biaxial directions from its original size. In some embodiments, the at least partial activation creates an expansion of the exemplary EAP film by 50%-1000% in a single axis or biaxial directions from its original size. In some embodiments, the activation creates an expansion of the exemplary EAP film by 100%-1000% in a single axis or biaxial directions from its original size. In some embodiments, the at least partial activation creates an expansion of the exemplary EAP film by 500%-1000% in a single axis or biaxial directions from its original size.

In some embodiments, variables that affect the expansion and the direction of the expansion include, but are not limited to:
  i) an amount and/or a direction of the pre-stretch;
  ii) an electrical charge being applied (e.g., from 10V-20,000V, from 100V-20,000V, from 1000V-20,000V, from 10V-1,000V, from 10V-10,000V, from 10,000V-20,000V);
  iii) a method and/or a type of fixation/attachment; and
  iv) any combination thereof.

In some embodiments, each conducting layer is attached to the sublayer of EAP film by, for example but not limited to, at least one of printing (e.g., utilizing conductive ink), etching (e.g., using a solution of electrolyte), brushing (e.g., using carbon graphite powder with silicon oil), water dispersion (e.g., using PAni based solution), gluing (e.g., gluing a laser cut or molded into an expanding pattern such as zigzag, rigid conducting sheet), and any other suitable applicable method(s).

In some embodiments, electro-active polymers that are pre-stretched improve conversion between electrical and mechanical energy. In some embodiments, the pre-stretch state/condition stabilizes the actuation of the electro-active polymer due to at least one of:
  i) minimizing or eliminating the pull-in instability by generating electrostriction;
  ii) increasing the breakdown strength; and
  iii) reducing the films thickness, which consequently lowers the voltages required for activation.

In some embodiments, reducing the films thickness is by stretching the material.

For example, the pull-in instability identifies a state, when voltage is applied on an electro-active polymer film, causing the film to thin down—e.g., voltage produces a higher electric field, which squeezes the electro-active polymer film as a positive feedback until an electrical breakdown.

In some embodiments, the voltage required to activated 3M VHB 4910 film, is 50 KV per 1 mm. Pre-stretching the film biaxially by 10, reduces the film thickness to 0.1 mm and the activation voltage to 5 KV). In some embodiments, when pre-stretched, acrylic copolymer elastomers (e.g., 3M VHB 4910 or VHB 4905 by 3M Corporation) produce a stable comparatively high and reversible electromechanical stretch of 3% to 1000% in area of the linear stretch.

In some embodiments of the present disclosure, the methods and apparatuses described herein can be configured to apply static compression, sequential compression, segmental compression, intermittent compression, or any other type of compression. In some embodiments, the methods and apparatuses described herein can be used for the prevention and or treatment for various vascular or lymphatic diseases, for example, but not limited to, DVT (Deep Vein Thrombosis), lymphedema, varicose veins, spider veins, CVI (Chronic Venous Insufficiency), ulcers, superficial venous thrombosis or phlebitis and diabetic wounds. In some embodiments, the active compression bandage can be used for the prevention and/or treatment and/or reduction of, for example, but not limited to, scar tissue, swelling, sore muscles, burn wounds, cellulitis, chronic edema, eczema, infected wounds and epidermolysis bullosa. In some embodiments, the methods and apparatuses described herein can be used to reduce the recovery time of orthopedic surgeries, swelling, infections and sport injuries. In some embodiments, the recovery time can be reduced by 1 to 100%, from 2 to 50%, from 4 to 25%, from 8 to 12%; from 9 to 10% and all ranges therebetween.

Some embodiments of the present disclosure relate to an apparatus comprising: at least two pre-stretched electro-active polymer ("EAP") layers. In some embodiments, each of the at least two pre-stretched EAP layers comprises a stretchable conductive coating disposed thereon.

In some embodiments, the apparatus comprises a plurality of first holders. In some embodiments, the plurality of first holders is positioned longitudinally relative to the at least two pre-stretched EAP layers, so that the plurality of first holders is sandwiched between the at least two pre-stretched EAP layers.

In some embodiments, the apparatus comprises a plurality of second holders. In some embodiments, the plurality of second holders is positioned latitudinally relative to each of the at least two pre-stretched EAP layers, so that the plurality of second holders is sandwiched between each of the at least two pre-stretched EAP layers.

Some embodiments of the present disclosure relate to a method comprising a step of: sandwiching a plurality of first holders between the at least two pre-stretched EAP layers. In some embodiments, the method comprises a step of: positioning the plurality of first holders longitudinally relative to the at least two pre-stretched EAP layers. In some embodiments, the method comprises a step of: sandwiching a plurality of second holders between each of the at least two pre-stretched EAP layers.

At least some aspects of the present disclosure will now be described with reference to the following numbered clauses, the clauses hereinafter designated as: ["C1, C2, C3, C4, etc. . . . "].

C1: An apparatus comprising: at least one composite film layer; wherein each of the at least one composite film layer comprises: a pre-stretched electro-active polymer ("EAP") sublayer; and a stretchable conductive sublayer disposed on the pre-stretched EAP sublayer; wherein the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state; wherein the stretchable conductive sublayer is configured to receive and distribute electrical current through the pre-stretched EAP sublayer while the pre-stretched EAP sublayer is maintained in the pre-stretched state; a plurality of first holders; wherein the plurality of first holders is positioned longitudinally relative to the at least one composite film layer, so that the plurality of first holders is attached on top the at least one composite film layer; a plurality of second holders; wherein the plurality of second holders is positioned latitudinally relative to each of the at least one composite film layer, so that the plurality of second holders is attach on top at least one composite film layer; wherein the plurality of first holders is disposed orthogonally relative to the plurality of second holders to define sections of a skeleton; wherein the skeleton is configured to maintain the pre-stretched EAP sublayer in the pre-stretched state, while allowing the sublayer to expand in one or two directions; at least one end grabbing portion; wherein the at least one end grabbing portion is disposed on a longitudinal end of at least one of the at least one composite film layer.

C2: The apparatus of C1, wherein the stretchable conductive sublayer are in the form of a predetermined pattern, wherein the predetermined pattern comprises: a series of latitudinally oriented sections; a plurality of longitudinal portions; wherein each longitudinal portion of the plurality of longitudinal portions connects each latitudinally oriented section of the series of latitudinally oriented sections to an adjacent latitudinally oriented section of the series of latitudinally oriented sections; wherein each longitudinal portion of the plurality of longitudinal portions is integral with each latitudinally oriented section of the series of latitudinally oriented sections; wherein each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections.

C3: The apparatus of C1 comprising two end grabbing portions disposed on opposed longitudinal ends of the apparatus.

C4: The apparatus of C1 comprising at least one extension portion integral to at least one of the least two composite film layers, wherein the at least one extension portion is configured to allow an electrical connection to an external power source.

C5: The apparatus of C1, further comprising at least one electrically insulating layer, wherein the at least one electrically insulating layer is disposed on an outer surface of each of the at least one composite film layer.

C6: The apparatus of C1 wherein the pre-stretched EAP sublayer is defined by an expansion in at least one of a latitudinal or a longitudinal direction, of from 1% to 5000% relative to an un-stretched EAP sublayer.

C7: The apparatus of C1, wherein the sufficiently flexible material of the stretchable conductive sublayer comprises at least one material chosen from: 1) a solution comprising: carbon or silver based conducting ink, Polyaniline (PAni), carbon, graphite powder, or any combination thereof; 2) carbon black powder, 3) conductive polymer, 4) conductive rubber, 5) conductive silver or carbon paste, 6) conductive epoxy, 7) conducting grease, 8) a laser cut or molded rigid conductive sheet in an expanding pattern, 9) a stretchable conductive sheet comprising networks of gold nano-particles, carbon nano-particles, or combinations thereof embedded in elastic polyurethane; or 10) any combination of the foregoing.

C8: A method comprising steps of: obtaining an apparatus comprising: at least one composite film layer; wherein each of the at least one composite film layer comprises: a pre-stretched electro-active polymer ("EAP") sublayer; and a stretchable conductive sublayer disposed on the pre-stretched EAP sublayer; wherein the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state; wherein the stretchable conductive sublayer is configured to receive and distribute electrical current through the pre-stretched EAP sublayer while the pre-stretched EAP sublayer is maintained in the pre-stretched state; a plurality of first holders; wherein the plurality of first holders is positioned longitudinally relative to the at least one composite film layer, so that the plurality of first holders is attached on top the at least one composite film layer; a plurality of second holders; wherein the plurality of second holders is positioned latitudinally relative to each of the at least one composite film layer, so that the plurality of second holders is attach on top at least one composite film layer; wherein the plurality of first holders is disposed orthogonally relative to the plurality of second holders to define sections of a skeleton; wherein the skeleton is configured to maintain the pre-stretched EAP sublayer in the pre-stretched state, while allowing the sublayer to expand in one or two directions; at least one end grabbing portion; wherein the at least one end grabbing portion is disposed on a longitudinal end of at least one of the at least one composite film layer; sending, with a controller, an electrical signal and a baseline voltage to a driver circuit; transforming, with the driver circuit, the baseline voltage into a sufficient voltage to at least partially electrically activate the composite film layer, and applying the at least partial activation voltage to the composite film layer, thereby at least partially electrically activating the EAP sublayer.

C9: The method of C8, further comprising steps of: wrapping the apparatus around a solid body; at least partially electrically activating the composite film layer to apply a first voltage to the EAP sublayer, wherein the application of the first voltage to the EAP sublayer applies a first pressure to the solid body, wherein the first pressure ranges from 6 mmHg to 1000 mmHg.

C10: The method of C9, further comprising a step of: applying a plurality of additional voltages to the EAP sublayer, wherein each additional voltage is different than the first voltage; wherein the application of each additional voltage to the solid body applies an additional pressure to the solid body, wherein each additional pressure is different from the first pressure.

C11: The method of C10, wherein the solid body is a solid body of variable stiffness, the method further comprising a step of: applying a plurality of additional voltages to the EAP sublayer; wherein the application of each additional voltage to the solid body applies an additional pressure to the solid body, wherein each additional pressure is the same as the first pressure, so as to compensate for the variable stiffness of the solid body.

C12: The method of C9, wherein the step of "at least partially electrically activating the EAP sublayer to apply a first voltage to the EAP sublayer," occurs before the step of "wrapping the apparatus around a solid body," the method further comprising a step of decreasing the voltage to a second voltage below the first voltage, so as to increase the pressure to a second pressure above the first pressure.

C13: The method of C8, wherein the partial activation voltage ranges from 10V to 20,000V.

C14: The method of C8, wherein the driver circuit is configured to measure a state of the pre-stretched EAP and transmit the state back to the controller.

C15: The method of C14, wherein the state of the pre-stretched EAP comprises at least one of: latitudinal expansion, longitudinal expansion, stretch, load, or functionality.

C16: A method comprising: mechanically stretching an electro-active polymer ("EAP") to form a pre-stretched EAP sublayer; applying, to the pre-stretched EAP sublayer, a solution comprising a flexible conductive material, thereby forming a stretchable conductive sublayer; applying an adhesive solution to the stretchable conductive sublayer; with the adhesive solution, adhering the stretchable conductive sublayer to the pre-stretched EAP sublayer to form a composite film layer; repeating the above steps at least one time, thereby forming at least one composite film layer; attaching a plurality of first holders on top the at least one composite film layer; positioning the plurality of first holders longitudinally relative to the at least one composite film layer; attaching a plurality of second holders on top of the at least one composite film layer; positioning the plurality of second holders latitudinally relative to the at least one composite film layer and orthogonally relative to the plurality of second holders to define sections of a skeleton and thereby maintain the pre-stretched EAP sublayer in the pre-stretched state, while allowing the sublayer to expand in one or two directions; and disposing at least one end grabbing portion on a longitudinal end of at least one of the at least one composite film layer thereby forming an EAP structure.

C17: The method of C16, wherein during the step of "applying, to the pre-stretched EAP sublayer, a solution comprising a flexible conductive material," the solution comprising the flexible conductive material is deposited onto the pre-stretched EAP sublayer according to a predetermined mask pattern, so that a shape of the stretchable conductive sublayer conforms to a shape of the predetermined mask pattern, wherein the predetermined mask pattern comprises: a series of latitudinally oriented sections; a plurality of longitudinal portions; wherein each longitudinal portion of the plurality of longitudinal portions connects each latitudinally oriented section of the series of latitudinally oriented sections to an adjacent latitudinally oriented section of the series of latitudinally oriented sections; wherein each longitudinal portion of the plurality of longitudinal portions is integral with each latitudinally oriented section of the series of latitudinally oriented sections; wherein each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections.

C18: The method of C16, further comprising a step of applying an electrically insulating layer to at least one surface of at least one composite film layers.

C19: The method of C16, further comprising a step of attaching to the EAP structure, at least one of: an extension configured to allow an electrical connection to an external power source, a driver circuit, a controller, a processor, or a signal generator.

C20: The method of C16, wherein during the step of "mechanically stretching the electro-active polymer to form a pre-stretched EAP sublayer," the EAP is stretched from 1% to 5000% in at least one of a latitudinal or longitudinal direction.

A person skilled in the art would understand that, without violating the principles of the present disclosure detailed herein, in some embodiments, the exemplary illustrative methods and the exemplary illustrative systems of the present disclosure can be specifically configured to be utilized in any combination with one or more techniques, methodologies, and/or systems detailed in U.S. Pat. No. 9,433,537 and/or WIPO Publication No. WO 2019/025854, each of such specific disclosures is incorporated herein by reference in its entirety for such purpose.

While several embodiments of the present disclosure have been described, it is understood that these embodiments are illustrative only, and not restrictive, and that many modifications may become apparent to those of ordinary skill in the art, including that the inventive methodologies, the inventive systems, and the inventive devices described herein can be utilized in any combination with each other. Further still, the various steps may be carried out in any desired order (and any desired steps may be added and/or any desired steps may be eliminated).

The invention claimed is:
1. An apparatus comprising:
at least one composite film layer;
    wherein each of the at least one composite film layer comprises:
        a pre-stretched electro-active polymer ("EAP") sublayer; and
        a stretchable conductive sublayer disposed on the pre-stretched EAP sublayer;
            wherein the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state;
            wherein the stretchable conductive sublayer is configured to receive and distribute electrical current while the pre-stretched EAP sublayer is maintained in the pre-stretched state;
a plurality of first holders;
    wherein the plurality of first holders is positioned longitudinally relative to the at least one composite film layer, so that the plurality of first holders is attached on top the at least one composite film layer;
a plurality of second holders;
    wherein the plurality of second holders is positioned latitudinally relative to each of the at least one composite film layer, so that the plurality of second holders is attach on top at least one composite film layer;
    wherein the plurality of first holders is disposed orthogonally relative to the plurality of second holders to define sections of a skeleton;

wherein the skeleton is configured to maintain the pre-stretched EAP sublayer in the pre-stretched state, while allowing the sublayer to expand in one or two directions;

at least one end grabbing portion;
wherein the at least one end grabbing portion is disposed on a longitudinal end of at least one of the composite film layers.

2. The apparatus of claim 1, wherein the stretchable conductive sublayer is in the form of a predetermined pattern, wherein the predetermined pattern comprises:
a series of latitudinally oriented sections;
a plurality of longitudinal portions;
wherein each longitudinal portion of the plurality of longitudinal portions connects each latitudinally oriented section of the series of latitudinally oriented sections to an adjacent latitudinally oriented section of the series of latitudinally oriented sections;
wherein each longitudinal portion of the plurality of longitudinal portions is integral with each latitudinally oriented section of the series of latitudinally oriented sections;
wherein each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections.

3. The apparatus of claim 1 comprising two end grabbing portions disposed on opposed longitudinal ends of the apparatus.

4. The apparatus of claim 1 comprising at least one extension portion integral to at least one of the least two composite film layers, wherein the at least one extension portion is configured to allow an electrical connection to an external power source.

5. The apparatus of claim 1, further comprising at least one electrically insulating layer, wherein the at least one electrically insulating layer is disposed on at least one of the outer surfaces of each of the at least one composite film layer.

6. The apparatus of claim 1 wherein the pre-stretched EAP sublayer is defined by an expansion in at least one of a latitudinal or a longitudinal direction, of from 1% to 5000% relative to an un-stretched EAP sublayer.

7. The apparatus of claim 1, wherein the sufficiently flexible material of the stretchable conductive sublayer comprises at least one material chosen from: 1) a solution comprising: carbon or silver based conducting ink, Polyaniline (PAni), carbon, graphite powder, or any combination thereof; 2) carbon black powder, 3) conductive polymer, 4) conductive rubber, 5) conductive silver or carbon paste, 6) conductive epoxy, 7) conducting grease, 8) a laser cut or molded rigid conductive sheet in an expanding pattern, 9) a stretchable conductive sheet comprising networks of gold nano-particles, carbon nano-particles, or combinations thereof embedded in elastic polyurethane; or 10) any combination of the foregoing.

8. A method comprising steps of:
obtaining an apparatus comprising:
at least one composite film layer; wherein each of the at least one composite film layer comprises:
a pre-stretched electro-active polymer ("EAP") sublayer; and
a stretchable conductive sublayer disposed on the pre-stretched EAP sublayer;
wherein the stretchable conductive sublayer comprises a sufficiently flexible material, such that the stretchable conductive sublayer is configured to conform to a size and shape of the pre-stretched EAP sublayer while the pre-stretched EAP sublayer is maintained in a pre-stretched state;
wherein the stretchable conductive sublayer is configured to receive and distribute electrical current through the pre-stretched EAP sublayer while the pre-stretched EAP sublayer is maintained in the pre-stretched state;
a plurality of first holders;
wherein the plurality of first holders is positioned longitudinally relative to the at least one composite film layer, so that the plurality of first holders is attached on top the at least one composite film layer;
a plurality of second holders;
wherein the plurality of second holders is positioned latitudinally relative to each of the at least one composite film layer, so that the plurality of second holders is attach on top at least one composite film layer;
wherein the plurality of first holders is disposed orthogonally relative to the plurality of second holders to define sections of a skeleton;
wherein the skeleton is configured to maintain the pre-stretched EAP sublayer in the pre-stretched state, while allowing the sublayer to expand in one or two directions;
at least one end grabbing portion;
wherein the at least one end grabbing portion is disposed on a longitudinal end of at least one of the at least one composite film layer;
sending, with a controller, an electrical signal and a baseline voltage to a driver circuit;
transforming, with the driver circuit, the baseline voltage into a sufficient voltage to at least partially electrically activate the composite film layer;
applying the at least partial activation voltage to the at least one composite film layer, thereby at least partially electrically activating the EAP sublayer.

9. The method of claim 8, further comprising steps of:
wrapping the apparatus around a solid body;
at least partially electrically activating the at least one composite film layer to apply a first voltage to the solid body;
wherein the application of the first voltage to the solid body applies a first pressure to the solid body, wherein the first pressure ranges from 6 mmHg to 1000 mmHg.

10. The method of claim 9, further comprising a step of:
applying a plurality of additional voltages to the at least one composite film layer
wherein each additional voltage is different than the first voltage;
wherein the application of each different voltage to the composite film layer applies a different pressure to the solid body.

11. The method of claim 10, wherein the solid body is a solid body of variable stiffness, the method further comprising a step of:
applying a plurality of voltages to the at least one composite film layer,
wherein each voltage of the plurality of voltages is different than the first voltage;

wherein the application of each additional voltage to the at least one composite film layer applies an additional pressure to the solid body, wherein each additional pressure is the same as the first pressure, so as to compensate for the variable stiffness of the solid body.

12. The method of claim 9, wherein the step of "electrically activating the composite film layer to apply a first voltage to the EAP sublayer," occurs before the step of "wrapping the apparatus around a solid body," the method further comprising a step of decreasing the voltage to a second voltage below the first voltage, so as to increase the pressure to a second pressure above the first pressure.

13. The method of claim 8, further comprising a step of at least partially activating the composite film layer to a partial activation voltage, wherein the activation voltage ranges from 10V to 20,000V.

14. The method of claim 8, wherein the driver circuit is configured to measure a state of the pre-stretched EAP and transmit the state back to the controller.

15. The method of claim 14, wherein the state of the pre-stretched EAP comprises at least one of: latitudinal expansion, longitudinal expansion, stretch, load, or functionality.

16. A method comprising:
mechanically stretching an electro-active polymer ("EAP") to form a pre-stretched EAP sublayer;
applying, to the pre-stretched EAP sublayer, a solution comprising a flexible conductive material, thereby forming a stretchable conductive sublayer;
applying an adhesive solution to the stretchable conductive sublayer;
with the adhesive solution, adhering the stretchable conductive sublayer to the pre-stretched EAP sublayer to form a composite film layer;
repeating the above steps at least one time, thereby forming at least one composite film layer;
attaching a plurality of first holders on top the at least one composite film layer;
positioning the plurality of first holders longitudinally relative to the at least one composite film layer;
attaching a plurality of second holders on top of the at least one composite film layer;
positioning the plurality of second holders latitudinally relative to the at least one composite film layer and orthogonally relative to the plurality of second holders to define sections of a skeleton and thereby maintain the pre-stretched EAP sublayer in the pre-stretched state, while allowing the sublayer to expand in one or two directions; and
disposing at least one end grabbing portion on a longitudinal end of at least one of the at least one composite film layer thereby forming an EAP structure.

17. The method of claim 16, wherein during the step of "applying, to the pre-stretched EAP sublayer, a solution comprising a flexible conductive material," the solution comprising the flexible conductive material is deposited onto the pre-stretched EAP sublayer according to a predetermined mask pattern, so that a shape of the stretchable conductive sublayer conforms to a shape of the predetermined mask pattern, wherein the predetermined mask pattern comprises:
a series of latitudinally oriented sections;
a plurality of longitudinal portions;
wherein each longitudinal portion of the plurality of longitudinal portions connects each latitudinally oriented section of the series of latitudinally oriented sections to an adjacent latitudinally oriented section of the series of latitudinally oriented sections;
wherein each longitudinal portion of the plurality of longitudinal portions is integral with each latitudinally oriented section of the series of latitudinally oriented sections;
wherein each longitudinal portion of the plurality of longitudinal portions has a width that is less than a width of each latitudinally oriented section of the series of latitudinally oriented sections, such that a plurality of latitudinally oriented spaces are formed between each latitudinally oriented section of the series of latitudinally oriented sections.

18. The method of claim 16, further comprising a step of applying an electrically insulating layer to at least one surface of at least one composite film layers.

19. The method of claim 16, further comprising a step of attaching to the EAP structure, at least one of: an extension configured to allow an electrical connection to an external power source, a driver circuit, a controller, a processor, or a signal generator.

20. The method of claim 16, wherein during the step of "mechanically stretching the electro-active polymer to form a pre-stretched EAP sublayer," the EAP is stretched from 1% to 5000% in at least one of a latitudinal or longitudinal direction.

* * * * *